(12) United States Patent
Yamakawa et al.

(10) Patent No.: US 12,220,266 B2
(45) Date of Patent: Feb. 11, 2025

(54) MEDICAL IMAGE PROCESSING APPARATUS AND MEDICAL IMAGE PROCESSING METHOD

(71) Applicant: FUJIFILM Healthcare Corporation, Kashiwa (JP)

(72) Inventors: Keisuke Yamakawa, Kashiwa (JP); Kazuki Matsuzaki, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 266 days.

(21) Appl. No.: 17/831,519

(22) Filed: Jun. 3, 2022

(65) Prior Publication Data

US 2022/0401042 A1 Dec. 22, 2022

(30) Foreign Application Priority Data

Jun. 17, 2021 (JP) .................................. 2021-100583

(51) Int. Cl.
*A61B 6/02* (2006.01)
*A61B 6/46* (2024.01)
*G06T 7/174* (2017.01)

(52) U.S. Cl.
CPC .............. *A61B 6/025* (2013.01); *A61B 6/463* (2013.01); *G06T 7/174* (2017.01);
(Continued)

(58) Field of Classification Search
CPC .............. G06T 11/008; G06T 2200/04; G06T 2207/10081; G06T 2207/10112;
(Continued)

(56) References Cited

U.S. PATENT DOCUMENTS 8,755,586 B2 * 6/2014 King ...................... A61B 6/037
  382/131
2005/0063611 A1 * 3/2005 Toki ..................... G01N 23/046
  382/299

(Continued)

FOREIGN PATENT DOCUMENTS

JP 2005-95329 A 4/2005
JP 2010-131371 A 6/2010
(Continued)

OTHER PUBLICATIONS

Japanese official action (and machine translation thereof) dated Jun. 4, 2024 in connection with Japanese Patent Application No. 2021-100583.

*Primary Examiner* — Dani Fox
*Assistant Examiner* — Soorena Kefayati
(74) *Attorney, Agent, or Firm* — Paul Teng (57) ABSTRACT

A medical image processing apparatus and a medical image processing method are provided which are capable of clearly presenting a distal end of a medical device in a tomosynthesis image of an object under examination into which the medical device is inserted. The medical image processing apparatus handles a tomosynthesis image generated using a plurality of projection images obtained by imaging an object under examination in an angle range of less than 180 degrees, and includes: a storage section for pre-storing blur data at individual imaging space coordinates; and a correction section for correcting the tomosynthesis image using the blur data.

14 Claims, 9 Drawing Sheets

(52) U.S. Cl.
CPC .............. *G06T 2200/04* (2013.01); *G06T 2207/10081* (2013.01); *G06T 2211/436* (2013.01)

(58) Field of Classification Search
CPC ..... G06T 2207/30021; G06T 2211/436; G06T 5/73; G06T 7/174; A61B 6/025; A61B 6/12; A61B 6/463; A61B 6/466
See application file for complete search history.

(56) References Cited

U.S. PATENT DOCUMENTS

| | | | |
|---|---|---|---|
| 2005/0133708 A1* | 6/2005 | Eberhard | A61B 6/025 250/234 |
| 2007/0237290 A1* | 10/2007 | Mostafavi | A61B 6/025 378/21 |
| 2010/0322493 A1* | 12/2010 | Wei | G06T 7/174 382/128 |
| 2011/0058647 A1* | 3/2011 | Star-Lack | G16H 50/30 378/65 |
| 2012/0033868 A1* | 2/2012 | Ren | A61B 6/502 378/21 |
| 2013/0202168 A1* | 8/2013 | Jerebko | G06T 11/006 382/131 |
| 2014/0363070 A1* | 12/2014 | Kobayashi | G06T 11/008 382/132 |
| 2016/0019701 A1* | 1/2016 | Visser | A61B 5/0059 378/19 |
| 2016/0071293 A1* | 3/2016 | Homann | G06T 15/08 382/131 |
| 2016/0089098 A1* | 3/2016 | Nakayama | A61B 6/467 600/424 |
| 2016/0140721 A1* | 5/2016 | Kawamura | G06T 7/593 382/132 |
| 2016/0166329 A1* | 6/2016 | Langan | A61B 6/4014 600/424 |
| 2017/0231593 A1* | 8/2017 | Fukuda | A61B 6/482 382/132 |
| 2020/0100752 A1* | 4/2020 | Morita | A61B 6/025 |
| 2020/0167917 A1* | 5/2020 | Douglas | A61B 6/463 |
| 2020/0170598 A1* | 6/2020 | Shea | A61B 6/5235 |
| 2020/0178909 A1* | 6/2020 | Morita | A61B 6/502 |
| 2020/0178926 A1* | 6/2020 | Kshirsagar | A61B 6/463 |
| 2020/0323510 A1* | 10/2020 | Maltz | A61N 5/1039 |

FOREIGN PATENT DOCUMENTS

| | | |
|---|---|---|
| JP | 2015-83082 A | 4/2015 |
| JP | 2016-67414 A | 5/2016 |
| JP | 2016-517789 A | 6/2016 |
| JP | 6502188 B2 | 4/2019 |

* cited by examiner

```
START
  ↓
ACQUIRE PROJECTION IMAGES — S301
  ↓
GENERATE TOMOSYNTHESIS IMAGE — S302
  ↓
READ BLUR DATA AT INDIVIDUAL IMAGING SPACE COORDINATES — S303
  ↓
CORRECT AND DISPLAY TOMOSYNTHESIS IMAGE — S304
  ↓
END
```

FIG. 4

| COORDINATES | BLUR DATA |
|---|---|
| (x1,y1,z1) | Blr_111 |
| (x2,y1,z1) | Blr_211 |
| ⋮ | ⋮ |
| (xn,yn,zn) | Blr_nnn |

| TYPE OF MEDICAL DEVICE | ADJUSTMENT COEFFICIENT |
|---|---|
| CATHETER | $\alpha 1$ |
| ENDOSCOPE | $\alpha 2$ |
| GUIDE SHEATH | $\alpha 3$ |
| ⋮ | ⋮ |

MEDICAL IMAGE PROCESSING APPARATUS AND MEDICAL IMAGE PROCESSING METHOD

CLAIM OF PRIORITY

The present application claims priority from Japanese Patent Application JP 2021-100583 filed on Jun. 17, 2021, the content of which is hereby incorporated by reference into this application.

BACKGROUND OF THE INVENTION

The present invention relates to a medical image processing apparatus and a medical image processing method in which medical images obtained by an X-ray tomosynthesis apparatus are handled and, more particularly, to technology to present clearly a distal end of a medical device which is inserted into an object under examination.

The X-ray tomosynthesis apparatus uses a plurality of projection images taken of an object under examination in many directions to generate tomosynthesis images which are tomographic images in a plane parallel to a bed. A three-dimensional image generated from a plurality of tomosynthesis images is used to identify the three-dimensional location of the medical device inserted into the object under examination such as a guide sheath or the like. On the other hand, the exposure dose from the X-ray tomosynthesis apparatus capturing a plurality of projection images is higher than that from a fluoroscopic X-ray apparatus. For the X-ray tomosynthesis apparatus, a reduction in exposure dose is desired.

Japanese Patent No. 6502188 discloses a reduction in exposure dose in tomosynthesis imaging in a manner to determine sizes and positions of a plurality of targets to be imaged, then to calculate an angular range in which the target to be imaged can be separated, and acquire projection images within the angular range.

In Japanese Patent No. 6502188, however, due consideration is not given to present clearly a distal end of a medical device inserted into an object under examination such as a catheter, an endoscope, or the like. In the X-ray tomosynthesis apparatus, the angular range within which the projection images are taken is limited to less than 180 degrees. This causes distortion in a tomosynthesis image to be generated, and therefore the distal end of the medical device will be blurred. If the distortion of the tomosynthesis image is large, the three-dimensional location of the distal end of the medical device cannot be identified, which in turn adversely affects medical treatment and the like.

SUMMARY OF THE INVENTION

It is accordingly an object of the present invention to provide a medical image processing apparatus and a medical image processing method which are capable of clearly presenting a distal end of a medical device in a tomosynthesis image of an object under examination into which the medical device is inserted.

To achieve the above object, an aspect of the present invention provides a medical image processing apparatus which handles a tomosynthesis image generated using a plurality of projection images captured in an angle range of less than 180 degrees. The medical image processing apparatus includes: a storage section for pre-storing blur data at individual coordinates of an imaging space; and a correction section for correcting the tomosynthesis image using the blur data.

Another aspect of the present invention provides a medical image processing method which handles a tomosynthesis image generated using a plurality of projection images taken in an angle range of less than 180 degrees. The medical image processing method includes: a reading step of reading blur data at individual coordinates of an imaging space; and a correction step of correcting the tomosynthesis image using the blur data.

According to the present invention, a medical image processing apparatus and a medical image processing method are provided, which allow a distal end of a medical device to be clearly presented in a tomosynthesis image of an object under examination into which the medical device is inserted.

DETAILED DESCRIPTION OF THE PREFERRED EMBODIMENTS

Embodiments of a medical image processing apparatus and a medical image processing method according to the present invention will now be described with reference to the accompanying drawings. It is noted that throughout the following description and the accompanying drawings, like reference signs are used to indicate components/elements having like functional configurations for the purpose of avoiding repeated description.

First Embodiment

Figure 1:
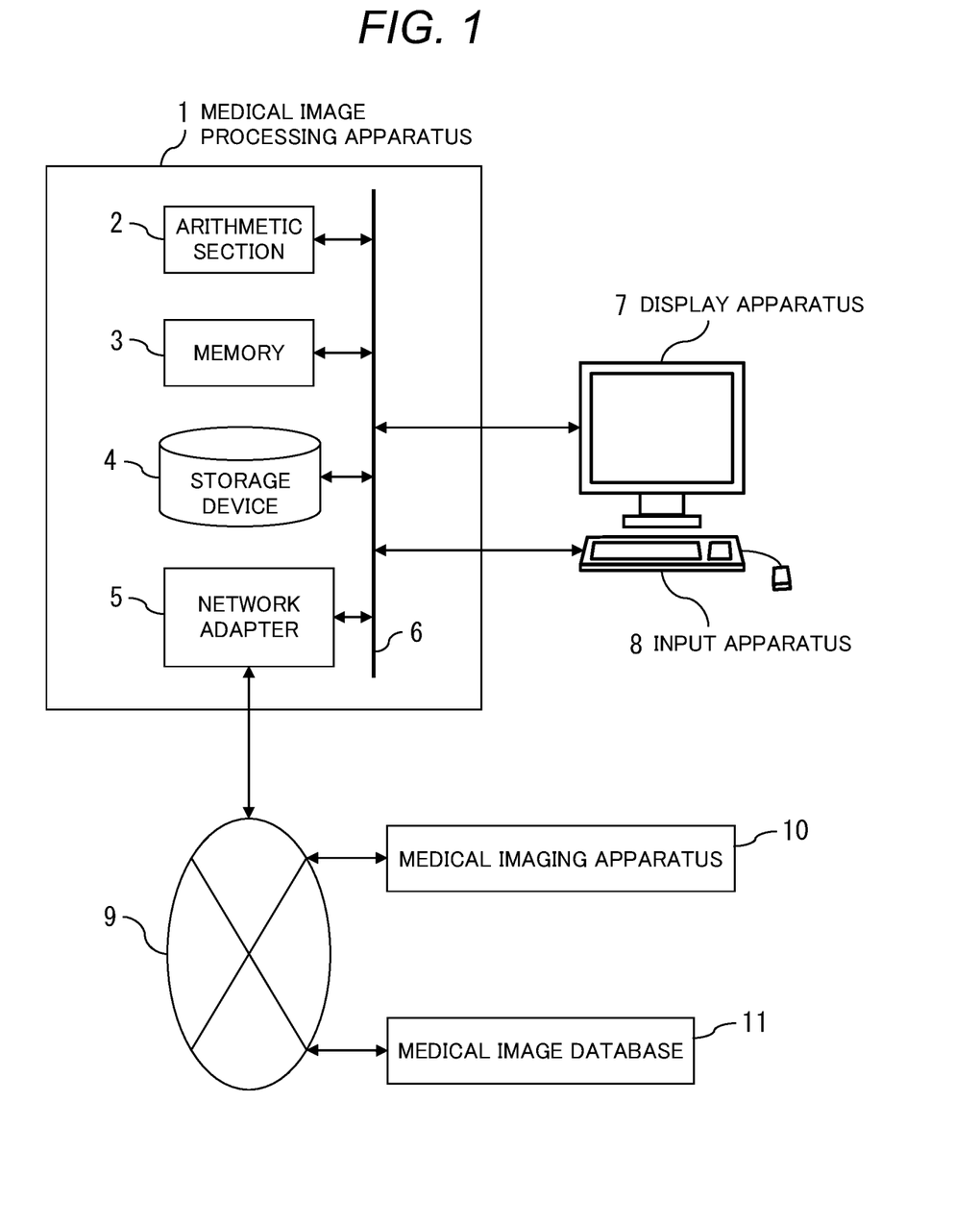
FIG. 1 is an overall configuration diagram of a medical image processing apparatus.

FIG. 1 is a diagram illustrating a hardware configuration of a medical image processing apparatus 1. The medical image processing apparatus 1 includes an arithmetic section 2, memory 3, a storage device 4, and a network adapter 5, which are interconnected therebetween through a system bus 6 such that they can transmit and receive signals. The medical image processing apparatus 1 is connected to a medical imaging apparatus 10 and a medical image database 11 via a network 9 such that they can transmit and receive signals. Further, the medical image processing apparatus 1 is connected to a display apparatus 7 and an input apparatus 8. As used herein, the phrase "can transmit and receive signals" expresses a condition in which signals can be electrically or optically sent/transmitted and received among them or from one to another irrespective of wired or wireless connection.

The arithmetic section 2 controls operation of each element, which specifically is CPU (Central Processing Unit), MPU (Micro Processor Unit), and/or the like. The arithmetic section 2 loads and executes programs and data required to execute the programs which are stored in the storage device 4, into the memory 3 in order to perform various types of image processing on medical images. The memory 3 stores the progress of a program and/or arithmetic processing which are executed by the arithmetic section 2. The storage device 4 stores programs executed by the arithmetic section 2 and data required to execute the programs, which specifically is HDD (Hard Disk Drive), SSD (Solid State Drive), and/or the like. The network adapter 5 connects the medical image processing apparatus 1 to the network 9 such as LAN, telephone lines, the Internet and/or the like. Various data handled by the arithmetic section 2 may be transmitted to and received from the exterior of the medical image processing apparatus 1 via the network 9 such as LAN (Local Area Network).

The display apparatus 7 displays processing results of the medical image processing apparatus 1, and the like, which specifically is a liquid crystal display and/or the like. The input apparatus 8 is an operation device through which an operator provides operation instructions to the medical image processing apparatus 1, which specifically is a keyboard, a mouse, a touch panel, and/or the like. The mouse may be replaced with another pointing device such as a track pad, a track ball, and the like.

The medical imaging apparatus 10 is an X-ray tomosynthesis apparatus that acquires, for example, a plurality of projection images taken of an object under examination in many directions and generates tomographic images from the plurality of projection images, which will be described later with reference to FIG. 2. The medical image database 11 is a database system that stores the projection images and the tomographic images acquired by the medical imaging apparatus 10, correction images obtained by performing image processing on the tomographic images, and the like.

Figure 2:
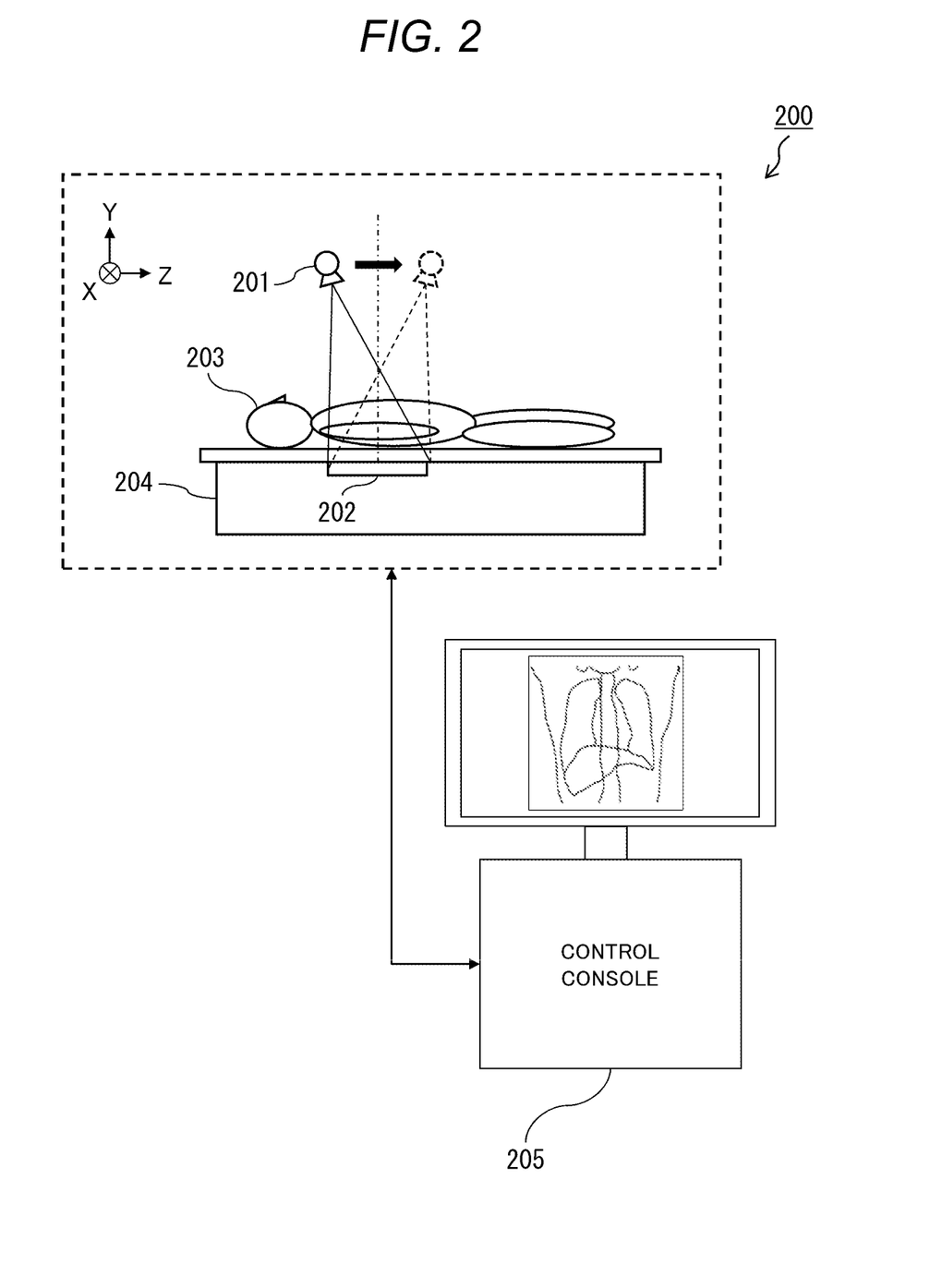
FIG. 2 is an overall configuration diagram of an X-ray tomosynthesis apparatus illustrated as an example of medical imaging apparatus.

With reference to FIG. 2, an overall configuration of an X-ray tomosynthesis apparatus 200 which is an example of the medical imaging apparatus 10 is described. In FIG. 2, a direction perpendicular to the plane of paper is defined as an X axis, the direction of the long side is defined as a Y axis, and the direction of the short side is defined as a Z axis. The X-ray tomosynthesis apparatus 200 includes an X-ray source 201, an X-ray detector 202, a bed 204, and a control console 205.

The X-ray source 201 irradiates with X rays the object 203 under examination laid on the bed 204. Upon the X-ray source 201 being applied with a high voltage depending on imaging conditions set via the control console 205, the object 203 under examination is irradiated with X rays.

The X-ray detector 202 detects the X rays passing through the object 203 under examination to measure spatial distribution of the passing X rays. The X-ray detector 202 is disposed on the opposite side from the X-ray source 201, and a plurality of detection elements are two-dimensionally arranged in the ZX plane. A two-dimensional projection image is generated based on a signal measured by the X-ray detector 202.

In order to obtain a plurality of projection images taken of the object 203 under examination in many directions, at least one of the X-ray source 201 and the X-ray detector 202 is moved in the Z axis direction. The plurality of projection images thus obtained are used to generate tomosynthesis images which are tomographic images in a plane parallel to the bed 204, i.e., in the ZX plane.

The control console 205 is apparatus for setting imaging conditions, generating tomosynthesis images, and performing display, which is configured with a so-called computer. On the control console 205 illustrated in FIG. 2, a chest tomosynthesis image of the object 203 under examination is displayed. The control console 205 may be the medical image processing apparatus 1 illustrated in FIG. 1.

In the X-ray tomosynthesis apparatus 200, the angle range within which projection images are taken is limited to less than 180 degrees, e.g., from 20 degrees to 40 degrees. This causes distortion in a tomosynthesis image to be generated, and the distal end of a medical device inserted into the object 203 under examination such as a catheter, an endoscope, or the like will be blurred. If the distortion of the tomosynthesis image is large, the three-dimensional location of the distal end of the medical device cannot be identified, which in turn adversely affects treatment and the like. To avoid this, in a first embodiment, the processing flow for producing a clear tomosynthesis image is executed.

Figure 3:
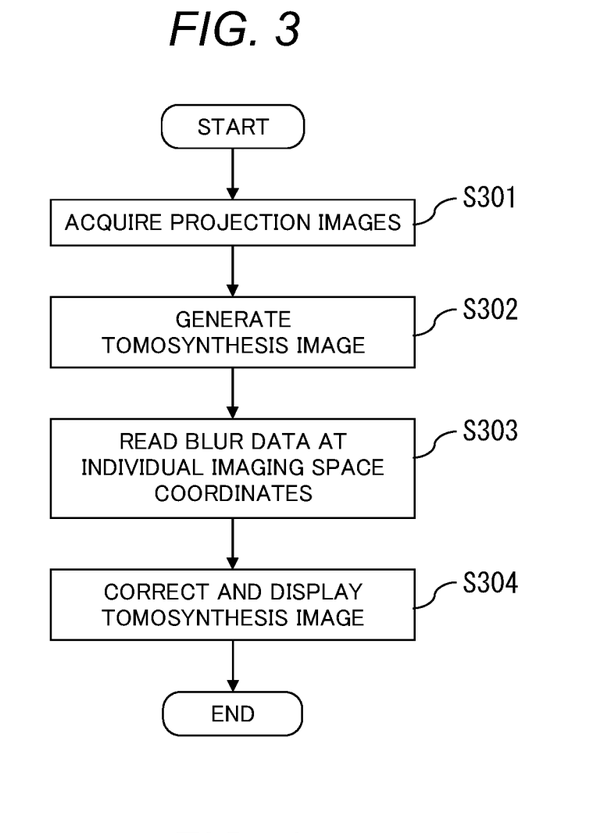
FIG. 3 is a flow diagram of an example of processing in a first embodiment according to the present invention.

With reference to FIG. 3, an example processing flow executed in the first embodiment is described for each step.
(S301)

The arithmetic section 2 acquires a plurality of projection images taken of an object 203 under examination in many directions. The arithmetic section 2 may receive projection images taken by the X-ray tomosynthesis apparatus 200 or may read projection images pre-stored in the storage device 4 or the medical image database 11.
(S302)

The arithmetic section 2 uses the plurality of projection images acquired at S301 to generate a tomosynthesis image.
(S303)

Figure 4:
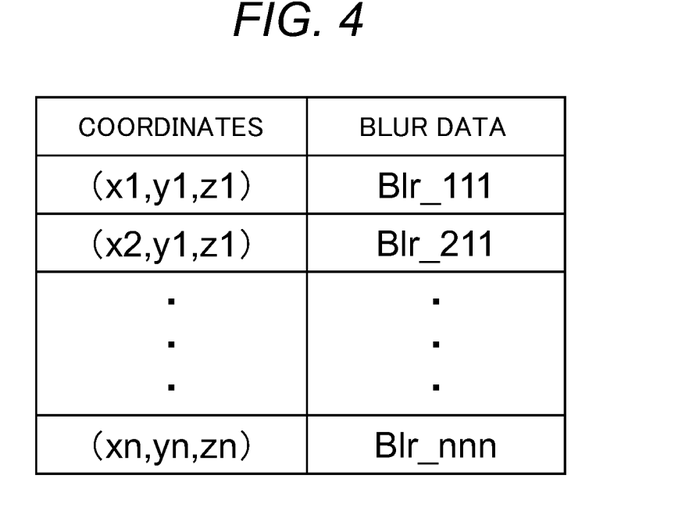
FIG. 4 is a diagram illustrating an example table in which blur data at individual imaging space coordinates is recorded.

The arithmetic section 2 reads blur data at individual imaging space coordinates. The blur data at individual coordinates is prestored in the storage device 4, for example, in table form as illustrated in FIG. 4. In the table illustrated in FIG. 4, the blur data is associated individually with three-dimensional coordinates. For example, blur data Blr_111 is associated with coordinates (x1, y1, z1), blur data Blr_211 is associated with coordinates (x2, y1, z1), and blur data Blr_nnn is associated with coordinates (xn, yn, zn).

The storage device 4 may also store a mathematical expression for calculating blur data from the imaging space coordinates. If a mathematical expression for calculating blur data is stored, the storage capacity of the storage device 4 can be saved.

It is noted that the blur data may be stored in the storage device 4 as Point Spread Functions (PSFs) generated by X-ray simulation or phantom imaging. For phantom imaging, a microspherical phantom of a size less than a comparable size of a pixel or coordinates of a point is used.
(S304)

The arithmetic section 2 corrects the tomosynthesis image generated in S302, using the blur data read in S303. Stated another way, the arithmetic section 2 functions as a correction section for correcting tomosynthesis images. For example, by performing the operation of deconvolution of PSFs at individual coordinates with the tomosynthesis image, the blurs included in the tomosynthesis image are corrected. The arithmetic section 2 causes the display apparatus 7 to display the corrected tomosynthesis image.

By the processing flow described above, the blurs included in the tomosynthesis image are corrected. This makes it possible to present clearly the distal end of the medical device inserted into the object under examination. As a result, treatment using the medical device cannot be adversely affected.

Second Embodiment

In the first embodiment, the correction of the tomosynthesis image using blur data at individual imaging space coordinates has been described. The correction using blur data corresponds to processing for enhancing high frequency components, and white noise and/or the like included in the tomosynthesis image may be enhanced and become obvious. To avoid this, a description in a second embodiment according to the present invention is given of limiting of the range in which the tomosynthesis image is corrected, in order to suppress the obvious existence of white noise and/or the like. The hardware configuration of medical image processing apparatus 1 in the second embodiment is identical with that in the first embodiment, and a description is omitted.

Figure 5:
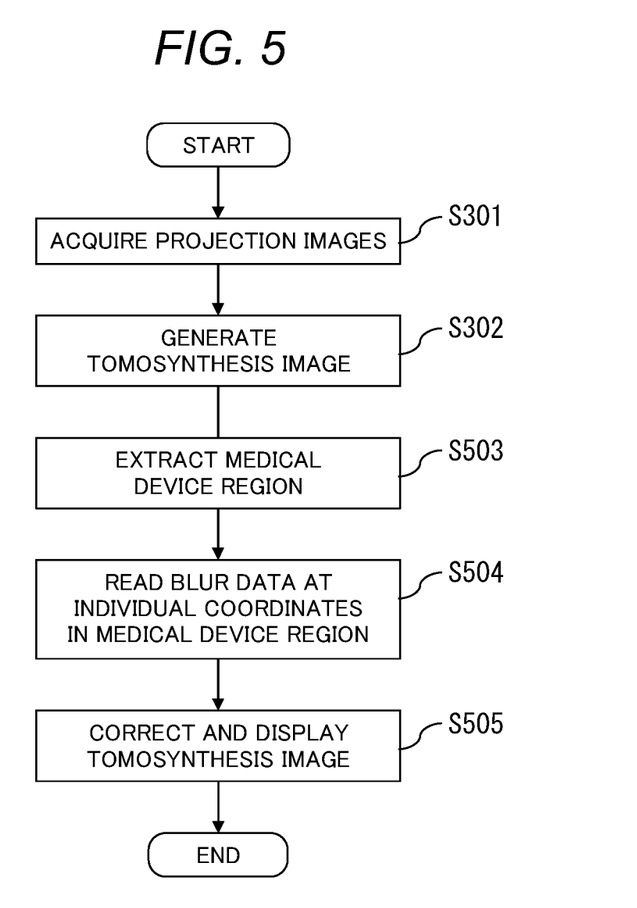
FIG. 5 is a flow diagram of an example of processing in a second embodiment according to the present invention.

With reference to FIG. 5, an example processing flow executed in the second embodiment is described for each step.

(S301)

As in the case of the first embodiment, the projection images are acquired.

(S302)

As in the case of the first embodiment, the tomosynthesis image is generated.

(S503)

The arithmetic section 2 extracts a medical device region from the tomosynthesis image generated in S302, the medical device region being a region of the medical device. Because the materials of the medical devices are known, a region in which the brightness values of the tomosynthesis image fall within a predetermined range may be extracted as a medical device region. Because the shapes of the medical devices are also known, a medical device region may be re-extracted based on shape similarity from the medical device regions which have been extracted based on the brightness values.

The medical device region may be extracted by using a machine learning engine that is generated by learning the tomographic images including the known medical device regions as teacher data. The machine learning engine is configured using, for example, CNN (Convolutional Neural Network). A tomographic image used as teacher data may be a tomosynthesis image or may be an X-ray CT image. However, when an X-ray CT image is used as the teacher data, the X-ray CT image has a higher spatial resolution, so that an improvement in accuracy with which the medical device region is extracted may be achieved.

Also, the position of the medical device region extracted from the tomosynthesis image may be modified based on the medical device region extracted from the projection images used for generation of the tomosynthesis image. The following is a description of specific steps: (1) a medical device region is extracted from each of the plurality of projection images used to generate the tomosynthesis image; (2) a forward projection operation is performed at a projection angle equal to that of each projection image on the medical device region extracted from the tomosynthesis image, in order to obtain forward projection data in which the medical device region is dummy projected; (3) a difference between the medical device region included in each piece of the forward projection data and the medical device region extracted from each projection image is calculated; and (4) if the calculated difference falls within a predetermined range, the procedure is ended, if it falls out of the predetermined range, the medical device region in the tomosynthesis image is corrected, and then the procedure returns back to step (2) to repeat steps (3) and (4). In short, the medical device region included in the tomosynthesis image is modified such that a difference between the forward projection data obtained by performing the forward projection operation on the medical device region extracted from the tomosynthesis image and the medical device region extracted from the projection images falls within a predetermined range.

(S504)

The arithmetic section 2 reads the blur data at individual coordinates in the medical device region extracted in S503 and its surrounding regions. The regions surrounding the medical device region extend to a predetermined number of pixels, e.g., three pixels from the boundaries of the medical device region.

(S505)

The arithmetic section 2 corrects the tomosynthesis image generated in S302 using the blur data read in S504. Specifically, the range in which the tomosynthesis image is corrected is limited to the medical device region and its surrounding regions. By limiting the correction range to the medical device region and its surrounding regions, the obvious existence of white noise and/or the like is suppressed.

Figure 6:
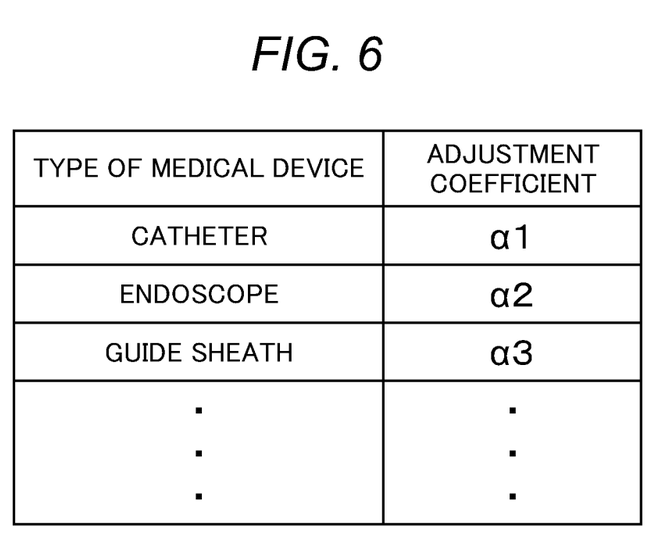
FIG. 6 is a diagram illustrating an example table in which adjustment coefficients are recorded for each type of medical devices.

The blur data used to correct the tomosynthesis image may be adjusted using an adjustment coefficient set depending on the type of the medical device. An X-ray attenuation coefficient varies depending on the type of the medical device, and thus the degree of blur also varies. To address this, the blur data may be adjusted depending on the type of the medical device. The adjustment coefficients for each type of medical device are stored in the storage device 4, for example, in table form as illustrated in FIG. 6. In the table illustrated in FIG. 6, an adjustment coefficient $\alpha 1$ is set for a catheter, an adjustment coefficient $\alpha 2$ is set for an endoscope, and an adjustment coefficient $\alpha 3$ is set for a guide sheath. The blur data is adjusted by being multiplied by an adjustment coefficient for each type of a medical device. A clearer media device region is produced by adjusting the blur data depending on the type of the medical device inserted into the object 203 under examination.

Figure 7:
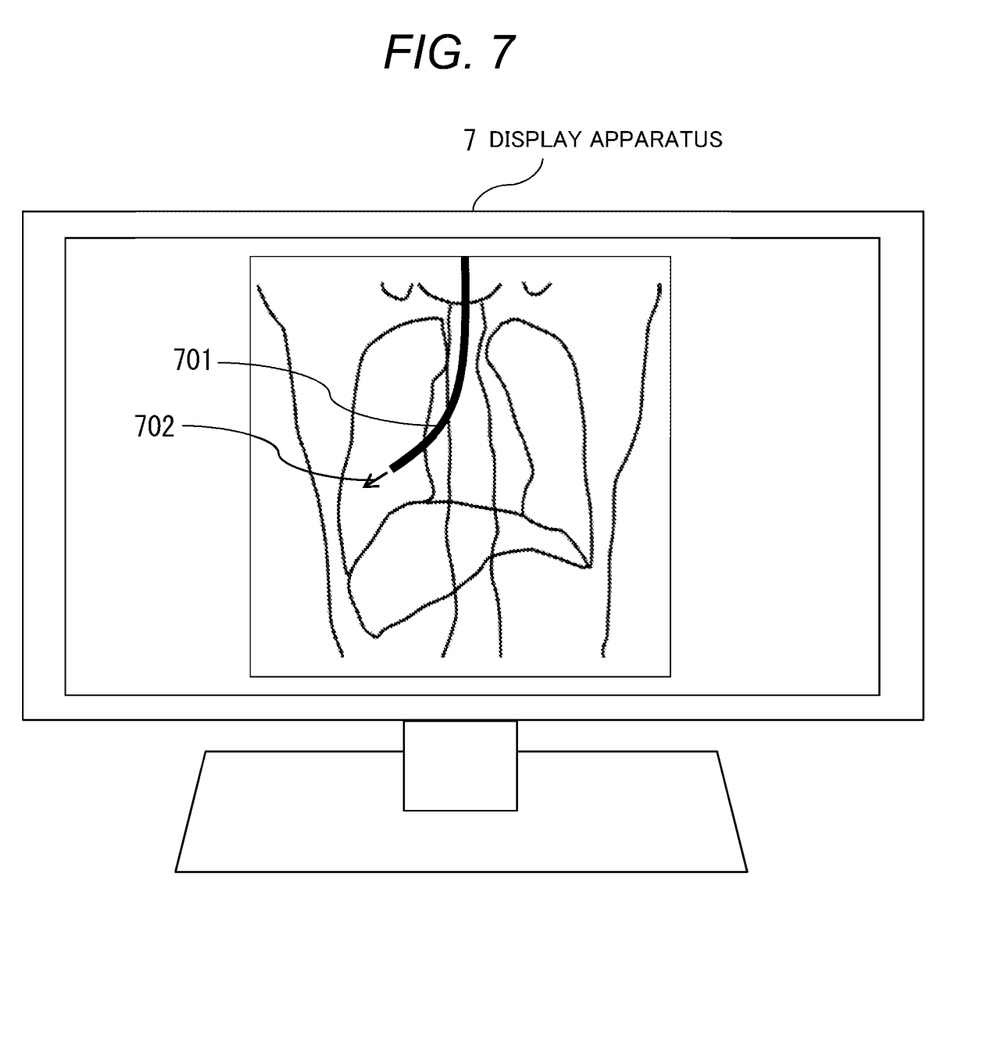
FIG. 7 is a diagram illustrating an example display window in the second embodiment.

The arithmetic section 2 causes the display apparatus 7 to display the corrected tomosynthesis image. FIG. 7 illustrates an example display window. In the display window illustrated in FIG. 7, the extracted medical device region 701 is superimposed and displayed on the tomosynthesis image of a chest, and an arrow 702 is also displayed to indicate the direction of movement of the medical device. The direction of movement of the medical device is calculated from the distal end and a bend of the medical device. The distal end and the bend of the medical device are obtained by performing the thinning processing on the medical device region 701. A three-dimensional shape of the extracted medical device region may be superimposed and displayed on a three-dimensional image generated from a plurality of tomosynthesis images.

By the processing flow described above, the blurs included in the tomosynthesis image are corrected. This makes it possible to present clearly the distal end of the medical device inserted into the object under examination. Also, because the correction range is limited to the medical device region and its surrounding regions, the obvious existence of white noise and/or the like is suppressed.

Instead of setting a range in which the tomosynthesis image is corrected based on the extracted medical device region, an adjustment coefficient set according to contrast of the tomosynthesis image may be used to adjust blur data, and then the blur data after the adjustment may be used to correct the tomosynthesis image. By adjusting the blur data by using the adjustment coefficient set according to contrast of a tomosynthesis image, the degree of correction is adjusted according to the contrast of the tomosynthesis image.

Figure 8:
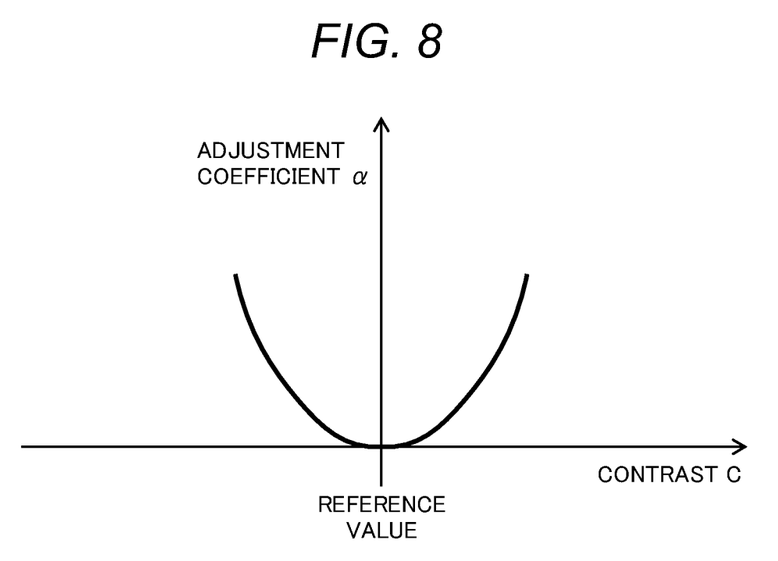
FIG. 8 is a diagram illustrating an example of the relationship between adjustment coefficients and contrast.

FIG. 8 illustrates an example of the relationship between adjustment coefficients α and contrast C. The adjustment coefficients α are exemplified in FIG. 8, which show a lowest value when the contrast C takes a reference value, and increase with the absolute value of the contrast C. The blur data at individual coordinates is adjusted by being multiplied by an adjustment coefficient α set according to the contrast C at the coordinates in question. That is, a clear media device region and clear surrounding regions thereof can be produced without extracting the medical device region.

Third Embodiment

In the first embodiment and the second embodiment, the correction of the tomosynthesis image generated using the acquired projection images has been described. If time resolution of the tomosynthesis image after correction is insufficient, treatment and/or the like may possibly be adversely affected. The time resolution means an exposure time required to generate the tomosynthesis image. In the case of the assumption that the X-ray source moves with constant velocity for exposure, the exposure time is in proportion to the number of projection images. The shorter the exposure time to the moving medical device, stated another way, the fewer the number of projection images, the smaller the misalignment of the medical device on the tomosynthesis image becomes. On the other hand, the longer the exposure time, stated another way, the larger the number of projection images, the larger the misalignment of the medical device on the tomosynthesis image becomes. To address this, a description in a third embodiment according to the present invention is given of selection of projection images to be used to generate a tomosynthesis image in order to display a tomosynthesis image with a time resolution required for misalignment of the medical device within an allowable range. The hardware configuration of the medical image processing apparatus 1 in the third embodiment is identical with that in the first embodiment, and a description is omitted.

Figure 9:
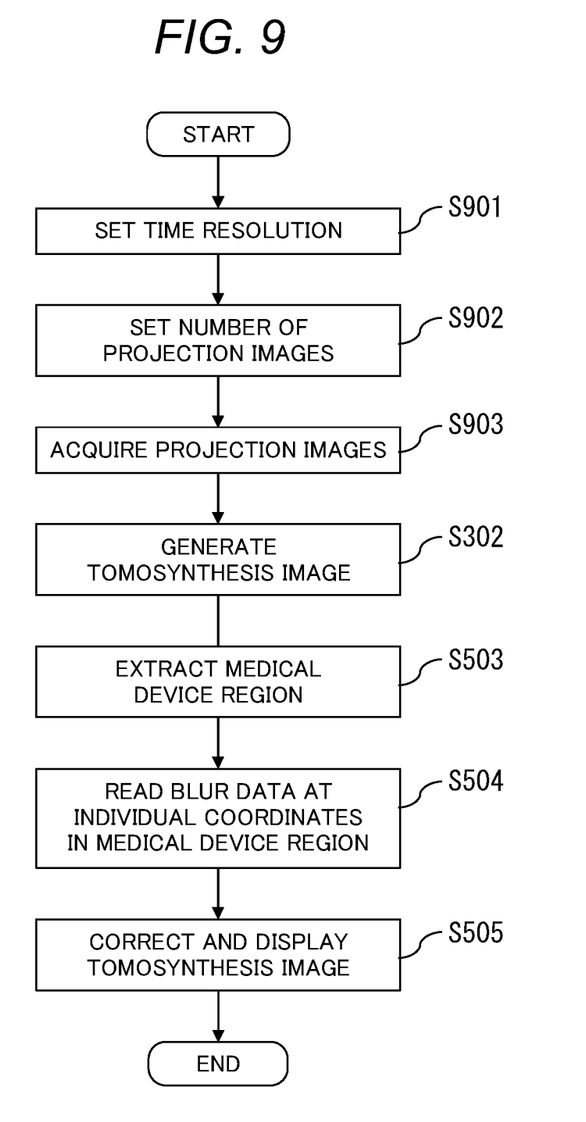
FIG. 9 is a flow diagram illustrating example processing in a third embodiment according to the present invention.

With reference to FIG. 9, an example processing flow executed in the third embodiment is described for each step.
(S901)
The arithmetic section 2 sets a time resolution. Stated another way, the arithmetic section 2 functions as a time resolution setting section.

Figure 10:
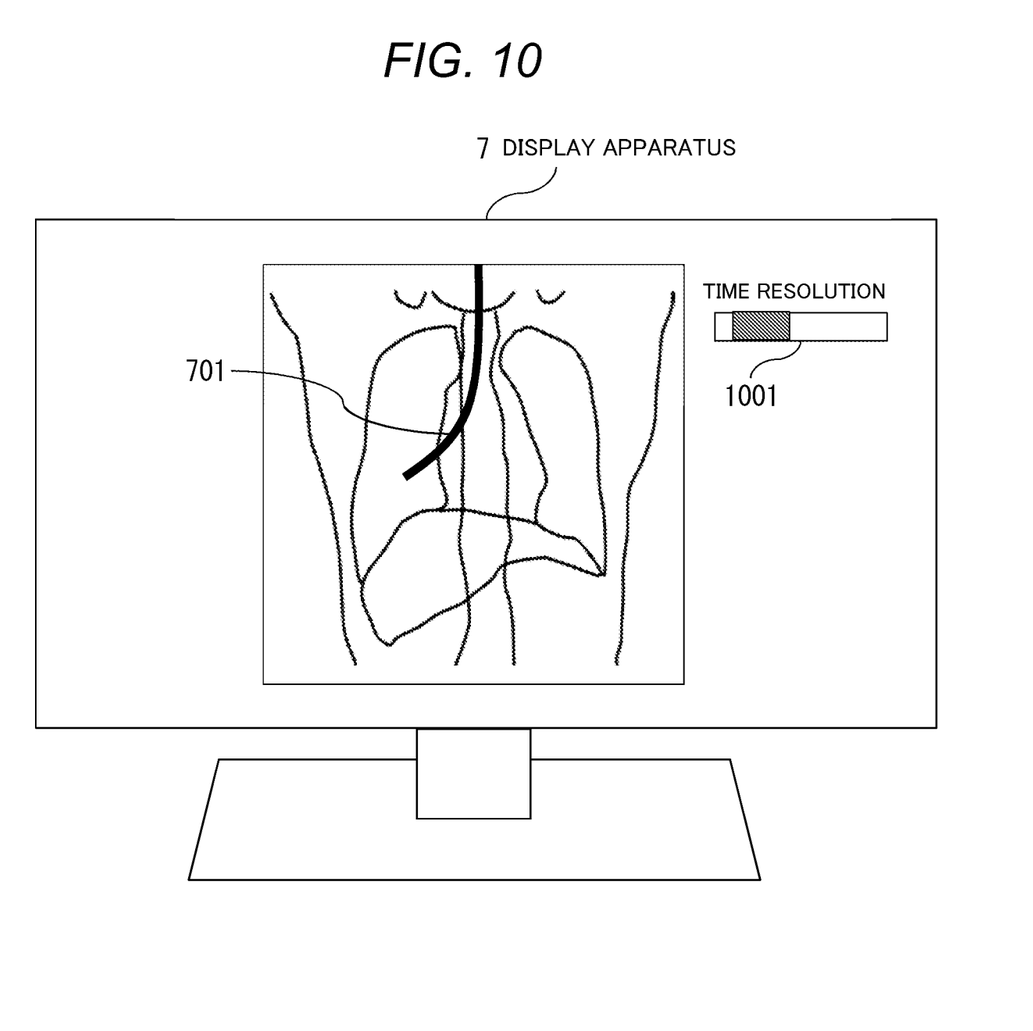
FIG. 10 is a diagram illustrating an example operation window in the third embodiment.

An operation window as illustrated in FIG. 10 may be used to set a time resolution. The operation window in FIG. 10 has a time resolution adjustment portion 1001. The time resolution adjustment portion 1001 is used by the operator adjusting the time resolution, and includes, for example, a slider bar and/or a text box.

The arithmetic section 2 may calculate a speed of the medical device from the fluoroscopic X-ray image taken prior to generation of a tomosynthesis image, and then set a time resolution based on the calculated speed. The higher the speed of the medical device, the higher the time resolution is set.
(S902)
Based on the time resolution set in S901, the arithmetic section 2 sets the number of projection images to be used for generation of a tomosynthesis image. The lower the time resolution set, the larger the number of projection images is set, whereas the higher the time resolution set, the smaller the number of projection images is set.
(S903)
The arithmetic section 2 acquires the number of projection images set in S902. The arithmetic section 2 may instruct the X-ray tomosynthesis apparatus 200 to capture the set number of projection images, or alternatively may read the set number of projection images from among the projection images pre-stored in the storage device 4 or the medical image database 11.
(S302)
As in the case of the first embodiment, the tomosynthesis image is generated.
(S503) As in the case of the second embodiment, a medical device region is extracted from the tomosynthesis image.
(S504)
As in the case of the second embodiment, the blur data at individual coordinates in the medical device region and its surrounding regions is read.
(S505)
As in the case of the second embodiment, the tomosynthesis image is corrected.

By the processing flow described above, the blurs included in the tomosynthesis image are corrected. This makes it possible to present clearly the distal end of the medical device inserted into the object under examination. Also, because the tomosynthesis image is generated by using the projection images selected according to the set time resolution, the tomosynthesis image with a required time resolution is displayed.

The embodiments according to the present invention have been described. It is to be understood that the present invention is not limited to the above embodiments and may be embodied by modifying elements thereof without departing from the spirit or scope of the present invention. Further, a plurality of elements disclosed in the above embodiments may be combined as appropriate. Further, several elements of all the elements described in the above embodiments may be omitted.

REFERENCE SIGNS LIST

1 . . . medical image processing apparatus
2 . . . arithmetic section
3 . . . memory
4 . . . storage device
5 . . . network adaptor
6 . . . system bus
7 . . . display apparatus
8 . . . input apparatus
10 . . . medical imaging apparatus
11 . . . medical image database
200 . . . X-ray tomosynthesis apparatus
201 . . . X-ray source
202 . . . X-ray detector
203 . . . object under examination 204 . . . bed
205 . . . control console
701 . . . medical device region
702 . . . arrow
1001 . . . time resolution adjustment portion

What is claimed is:

1. A medical image processing apparatus which handles a tomosynthesis image generated using a plurality of projection images obtained by imaging an object under examination in an angle range of less than 180 degrees, the medical image processing apparatus comprising:
   a storage section for pre-storing blur data at individual coordinates of an imaging space; and
   a correction section for correcting the tomosynthesis image using the blur data, wherein
   the correction section extracts, from the tomosynthesis image, a medical device region as a region of a medical device inserted into the object under examination, and based on the medical device region, the correction section sets a range in which the tomosynthesis image is corrected.

2. The medical image processing apparatus according to claim 1, wherein the correction section calculates a direction of movement of the medical device.

3. The medical image processing apparatus according to claim 1, wherein the correction section extracts the medical device region by using a machine learning engine generated by learning, as teacher data, tomographic images including known medical device regions.

4. The medical image processing apparatus according to claim 1, wherein the correction section modifies the medical device region such that a difference between forward projection data and a medical device region extracted from the projection images falls within a predetermined range, the forward projection data being obtained by performing forward projection operation on the medical device region.

5. The medical image processing apparatus according to claim 1, wherein the correction section adjusts the blur data by using an adjustment coefficient set depending on a type of a medical device inserted into the object under examination, and corrects the tomosynthesis image by using the blur data thus adjusted.

6. The medical image processing apparatus according to claim 2, wherein the correction section calculates a three-dimensional shape of the medical device.

7. The medical image processing apparatus according to claim 3, wherein the teacher data includes X-ray CT images.

8. A medical image processing apparatus which handles a tomosynthesis image generated using a plurality of projection images obtained by imaging an object under examination in an angle range of less than 180 degrees, the medical image processing apparatus comprising:
   a storage section for pre-storing blur data at individual coordinates of an imaging space; and
   a correction section for correcting the tomosynthesis image using the blur data,
   wherein the correction section adjusts the blur data by using an adjustment coefficient set according to contrast of the tomosynthesis image, and corrects the tomosynthesis image by using the blur data thus adjusted.

9. A medical image processing apparatus which handles a tomosynthesis image generated using a plurality of projection images obtained by imaging an object under examination in an angle range of less than 180 degrees, the medical image processing apparatus comprising:
   a storage section for pre-storing blur data at individual coordinates of an imaging space;
   a correction section for correcting the tomosynthesis image using the blur data; and
   a time resolution setting section for setting a time resolution of the tomosynthesis image,
   wherein the correction section corrects a tomosynthesis image generated using a set number of projection images based on the time resolution.

10. The medical image processing apparatus according to claim 9, wherein the time resolution setting section accepts a time resolution input via an input apparatus.

11. The medical image processing apparatus according to claim 9, wherein the time resolution setting section uses fluoroscopic X-ray images taken prior to generation of the tomosynthesis image to calculate a speed of the medical device inserted into the object under examination, and then sets the time resolution based on the calculated speed.

12. A medical image processing method comprising:
   a reading step of reading blur data at individual coordinates of an imaging space;
   a correction step of correcting, using the blur data, a tomosynthesis image which was generated using a plurality of projection images taken in an angle range of less than 180 degrees, the correction step correcting a limited range in the tomosynthesis image; and
   extracting, from the tomosynthesis image, a medical device region as a region of a medical device inserted into the object under examination, and based on the medical device region, setting a range in which the tomosynthesis image is corrected.

13. A medical image processing method comprising:
   a reading step of reading blur data at individual coordinates of an imaging space;
   a correction step of correcting, using the blur data, a tomosynthesis image which was generated using a plurality of projection images taken in an angle range of less than 180 degrees, the correction step correcting a limited range in the tomosynthesis image; and
   adjusting the blur data by using an adjustment coefficient set depending on a type of a medical device inserted into the object under examination, and correcting the tomosynthesis image by using the blur data thus adjusted.

14. A medical image processing method comprising:
   a reading step of reading blur data at individual coordinates of an imaging space;
   a correction step of correcting, using the blur data, a tomosynthesis image which was generated using a plurality of projection images taken in an angle range of less than 180 degrees, the correction step correcting a limited range in the tomosynthesis image; and
   adjusting the blur data by using an adjustment coefficient set according to contrast of the tomosynthesis image, and correcting the tomosynthesis image by using the blur data thus adjusted.

* * * * *